United States Patent
Hill et al.

[11] Patent Number: 6,067,846
[45] Date of Patent: May 30, 2000

[54] APPARATUS AND METHOD FOR TESTING THE HARDNESS OF A PIPE

[76] Inventors: Jack O. Hill, 14515 Wunderlich, Apt. 1111, Houston, Tex. 77069; Leroy Fry, Jr., 17707 Theisswood Ct., Spring, Tex. 77379

[21] Appl. No.: 09/301,752

[22] Filed: Apr. 29, 1999

Related U.S. Application Data

[63] Continuation-in-part of application No. 08/958,515, Oct. 27, 1997, abandoned.

[51] Int. Cl.[7] ....................................... G01N 3/42
[52] U.S. Cl. ................................................. 73/82
[58] Field of Search .................... 73/78, 81, 82, 73/865.8

[56] References Cited

U.S. PATENT DOCUMENTS

| | | | |
|---|---|---|---|
| 4,196,616 | 4/1980 | Argabrite et al. | 73/81 |
| 4,791,807 | 12/1988 | Oechsle | 73/81 |
| 4,974,443 | 12/1990 | Heitmann | 73/81 |
| 5,315,879 | 5/1994 | Crochon et al. | 73/81 |

FOREIGN PATENT DOCUMENTS 0171243  10/1982  Japan ......................... 73/78

*Primary Examiner*—Robert Raevis
*Attorney, Agent, or Firm*—Harrison & Egbert

[57] ABSTRACT

An apparatus for testing hardness of a pipe including a body having a longitudinal axis, a probe connected to the body and extending transverse to the longitudinal axis of the body, a retaining mechanism connected to the probe and positioned within the body so as to maintain the probe in a fixed position relative to the pipe while the body is moving through the pipe, and a processor connected to the probe so as to convert a signal produced by the probe relative to the hardness of the pipe into a humanly perceivable indication of pipe hardness. The probe serves to contact a point along the inner surface of the pipe while the body is moving continuously through the pipe.

18 Claims, 5 Drawing Sheets

6,067,846

APPARATUS AND METHOD FOR TESTING THE HARDNESS OF A PIPE

RELATED APPLICATION

The present application is a continuation-in-part of U.S. patent application Ser. No. 08/958,515, filed on Oct. 27, 1997, now abandoned, and entitled "APPARATUS AND METHOD FOR TESTING THE HARDNESS OF A PIPE", presently pending.

TECHNICAL FIELD

The present invention relates to pipeline inspection devices. More particularly, the present invention relates to pipe inspection pigs which serve to detect the hardness of the pipe at specific locations.

BACKGROUND ART

Numerous pipe inspection pigs are in existence and have been used in connection with non-destructive inspection of pipelines for gaseous or liquid materials, such as natural gas, liquid hydrocarbons, or water.

Various methods of detecting flaws or defects from the inside of a pipe or pipeline have been attempted with varying degrees of success. Ferromagnetic induction devices have been used as disclosed in U.S. Pat. No. 4,742,298. This invention was directed to determining the presence and the magnitude of surface flaws and to overcoming difficulties encountered in determining the presence and the magnitude of surface flaws in a pipe. The solution proposed was to use a cylindrical primary alternating current coil which is coaxially aligned with the pipe to generate a high frequency AC magnetic field in the pipeline, a multiple cylindrical secondary AC sensing coil where arranged at prescribed intervals in a circumferential direction around the interior of the pipe, each secondary coil having an axis parallel to the axis of the primary coil. The AC voltage sensed at each secondary coil is set to be proportional to the density of a parallel component of magnetic flux caused by the AC magnetic field generator.

Eddy current sensing probes have also been used primarily in connection with non-destructive inspection and testing of relatively thin-walled tubing which is not ferromagnetic material. Such tubing does exist in steam generators and heating exchangers having been the primary focus of eddy current probes as disclosed in U.S. Pat. No. 4,851,773 which discloses a single direction rotating head profilometer. One embodiment of that device discloses an electromechanical eddy current probe having a rotatable sensing head for sensing the wall thickness and for locating local defects in a tube or conduit through which it is passed. Basically, the mechanical profilometer probe was designed to detect dents in the interior surface of steam generator tubes. The position of the rotating head is varied along the length of the tubing being inspected as the probe is drawn through the tubing with a cable.

Another eddy current probe is disclosed in U.S. Pat. No. 4,952,875 in which a plurality of pairs of diametrically opposed sensing coils are alternatingly staggered along the longitudinal axis of the test sensor to give complete coverage of the interior pipe surface and are further permitted to move in and out to accommodate the size differences or constrictions in the pipeline. However, the sensor probe is intended to move longitudinally through the pipeline.

Also, U.S. Pat. No. 5,068,608 discloses multiple coil eddy current probe system and an eddy current probe is disclosed in which a defect is first detected when the probe is positioned adjacent the defect and a series of axially spaced probes are activated to sense and detect the extremities of a crack or other discontinuity. Generally, eddy current probes have not been particularly successful with respect to underground pipelines constructed of steel or other ferromagnetic materials and having pipeline walls with thicknesses substantially greater than the normal eddy current penetration depth. However, one attempt to provide an eddy current probe or ferromagnetic pipeline flaw detection was disclosed in U.S. Pat. No. 4,107,605.

The most popular and currently most useful sensors for ferromagnetic pipeline inspection have been magnetic flux generators and magnetic flux leakage sensors which are positioned circumferentially around an inspection pig which is moved longitudinally through the pipeline. Examples of such sensors are disclosed in U.S. Pat. Nos. 4,105,972, 4,310,796, 4,444,777 and 4,458,601. The operation of such magnetic flux detection probes is described in U.S. Pat. No. 4,789,827 in connection with a magnetic flux detection probe in which the sensors are intentionally spaced at different radial distances or spaced at different distances from the interior pipe surface in an effort to obtain greater accuracy with respect to the location of the flaw or defect on the inside or the outside of the pipe wall.

Some attempts have been made to detect defects at different angular orientations in connection with testing and inspecting pipes as they are being manufactured. U.S. Pat. No. 3,906,357 discloses an exterior pipe testing device in which there are two external sensor sections, one having a plurality of fixed sensing shoes circumferentially spaced around the pipe to be inspected which depends upon linear movement of the pipe therethrough for detecting flaws or defects primarily oriented circumferentially around the pipe. A second inspection unit is provided which has a pair of opposed magnetic sensing shoes which is rotated rapidly around the outside of the pipe to be inspected in an effort to detect longitudinal cracks which might otherwise go unnoticed with the fixed shoe sensing unit. Complex circuitry is used to coordinate the sensor input from each of the sensing units with a rotating magnetic pulse generator geared to the linear motion of the pipe being manufactured. A purpose of this device is to actuate one or more spray cans at the linear and the circumferential position where a manufacturing flaw is detected either by the linear inspection unit or the rotary inspection unit. Application of such a testing device to on-site underground pipelines has not been demonstrated.

Another exterior pipe testing device has been disclosed in U.S. Pat. No. 4,439,730, in which pairs of north and south poles of magnets are held adjacent to the exterior wall of a pipe at uniformly spaced apart positions circumferentially around the pipe. The north and south poles are positioned between the north and south poles of longitudinally spaced apart circular magnets around the pipe. The circumferential spaced apart magnets are rotated at a high rate of speed so that orthogonically directed resultant magnetic field is produced on opposite sides of the pipe between the north and south pole of the rotating magnets. Pairs of flux detectors are interposed on opposite sides of the rotating magnet. The magnets are rotated at a sufficiently high rate of speed relative to the longitudinal motion of the pipe since the flux field interruptions in the same incremental area of the pipe. Again, complex circuitry is required in order to coordinate the sensor input from each of the sensing units because of the high rotational speed (320 revolutions per minute in the example set forth in '730) in order to keep track of the sampled signals from the two overlapping sensors and further, to coordinate them to a longitudinal position along the pipe. At a longitudinal travelling speed of 80 feet per minute as set forth in the example, the device must make four complete revolutions during every one foot of travel, which is consistent with the sensor field slightly over three inches long, so that 100% of the pipe surface can be covered.

Pipeline flaw detectors for use inside of existing pipelines have also provided rotary mechanisms for rotating sensing shoes helically through the pipeline as the detector is moved linearly therealong. One such device is disclosed in U.S. Pat. No. 3,238,448 which, upon detecting a flaw, actuates a strong electromagnet to magnetize the corresponding portion of the pipeline so that the position of the defect can be detected from aboveground with magnetic sensors. This device rotates two opposed search units in a single direction such that only very large flaws can be accurately detected and locating any such detected flaws is dependent upon a second careful searching action for the magnetized pipe section from above ground.

Another pipeline inspection apparatus is disclosed in U.S. Pat. No. 4,072,894 which produces a circumferentially directed magnetic flux field as flux leakage detection sensors are resiliently held against the pipe wall surface and helically moved through the pipe to pass transversely across any longitudinally extending anomalies in the pipe wall.

One of the most popular and currently the most widely used state-of-the-art internal magnetic flux gas pipe inspection devices comprises a pipeline pig which has sealing cups around the exterior perimeter to both center the apparatus and to drive it by differential gas pressure along the pipeline. A magnetic flux is generated by multiple circumferentially spaced magnets with north and south poles axially spaced apart and a magnetic flux sensor interposed therebetween. In operation, the pig travels linearly through the pipeline and sensory input data from each sensor is recorded as a function of distance of travel. When a defect, void, or other anomaly in the pipe is indicated by sensing an interruption of a smooth longitudinal magnetic flux, then such an anomaly is recorded on a graph as a function of time or distance. A major drawback of this device is that the longitudinal, or axially aligned, magnetic flux cannot always detect longitudinal voids or defects such as a uniform deterioration along a continuous welded seam of the pipeline. Resolution is determined by the size of the multiple sensor unit. A second set of circumferentially positioned magnetic flux generators and flux leakage sensors can be positioned at a small staggered distance with respect to the first set so that the space between the flux generator and sensor shoes is covered by the second set of sensors.

One of the regulations that both state and federal agencies have is a requirement that each length (joint) of pipe installed in a pipeline be documented as to the "grade" of steel used in the making of the joint of pipe. The records of many pipelines have been lost or poorly kept. The Federal Department of Transportation (DOT) has, as of 1997, given the pipeline owners five years to bring their records into compliance. Line pipe is identified by size, wall thickness and grades. Intelligent pigs, as described hereinbefore, presently measure thickness, joint length, geographic position and other physical parameters. Pipe grade is controlled by the steel mill which produces the pipe. It is confirmed by testing. The grade can be confirmed by pressure tests and tensile tests. Over the years, mill records for joints of pipe may be lost and/or undocumented joints may be placed in the pipeline. Should a pipeline contain one or more undocumented pipe joints, the DOT regulations require that the pipeline be operated at pressures assuming the pipe grade is 24,000 p.s.i. This would require that many pipelines lower their operating pressure to uneconomical levels. Many pipelines in the U.S. are operating in excess of the legal allowable pressures.

In order to "document" the grade of the pipe joints, two techniques can be employed. First, coupons may be cut from the line at various intervals. These coupons are then tested by pulling to yield so as to determine tensile strength. This method requires that the line must be removed from service. As such, this is a costly approach. Furthermore, this method can produce damage which may accelerate pipeline failure.

An alternative technique is to show that the pipe is of the grade the pipeline is rated at by a preponderous of evidence. To establish the grade of the pipeline, it is important to note that grades of pipe made at approximately the same time (year) have the same basic properties of: (1) chemical composition; (2) density (velocity of sound); (3) magnetic (eddy current field) and (4) hardness (Vickers B indentation). By measuring one or more of these properties in a documented joint of pipe in a line, other joints can be compared to this "standard". In this manner, each joint can be confirmed to be the same or different than the "standard" joints of pipe. This method allows for an intelligent inspection tool (i.e. the pig) to be designed to compare the grade of each joint of pipe. When coupled with the information from another tool, such as a Geopig, its location in the pipeline, its geodetic position, and the grade of each joint can be verified.

Presently, tests of density (speed of sound), and magnetism (conductivity) can be achieved with the pigs of the prior art, as described herein previously. A hardness test may be made with a MICRODUE (MIC 10). This established hardness tester operates according to the ultrasonic contact impedance method. This method enables quick and easy measurements by positioning the probe and reading off the value. This operational ease is achieved because Vickers diamond indent in the material's surface is electronically measured and instantly displayed as a hardness value without using the cumbersome optical evaluation of the microscope normally associated with Vickers hardness testing. The MIC 10 is a very easy instrument to use. It is a hardness tester that can be transported anywhere for testing components at any location. The small narrow probe can even enable one to make measurements at positions that are difficult to access, such as tooth flanks or roots of gears. It can be measured in any direction, e.g. in the horizontal or overhead position. In order for the MIC 10 probe to be properly used, it must remain relatively static relative to the item to be tested for a short time, i.e. 30 milliseconds. Once the reading is obtained, the data can be transmitted via an RS232C port to a master data memory located at a desired location.

It is an object of the present invention to prove a method and apparatus for the testing of the hardness of an interior surface of a pipeline.

It is another object of the present invention to prove a method and apparatus which allows an MIC 10 probe to momentarily remain static during the movement of a pig through the pipeline.

It is a further object of the present invention to prove a method and apparatus which facilitates the determination of the grade of the pipeline by a preponderance of evidence.

It is a further object of the present invention to prove a method and apparatus for the measurement of the hardness of a pipe which allows for the documentation of the grade of pipe joints.

It is still a further object of the present invention to prove a method and apparatus for the measurement of pipeline hardness which is easy to use, easy to install, easy to manufacture, and relatively inexpensive.

These and other objects and advantages of the present invention will become apparent from a reading of the attached specification and appended claims.

SUMMARY OF THE INVENTION

The present invention is an apparatus for testing the hardness of a pipe which comprises a body having a longitudinal axis, a probe connected to the body and extending transverse to the longitudinal axis, a retention device connected to the probe and positioned within the body so as to maintain the probe in a fixed position relative to the pipe while the body is moving in the pipe, and processor connected to the probe so as to convert the signal from the probe into a humanly perceivable indication of pipe hardness. The probe serves to contact the inner surface of the pipe so as to produce a signal relative to the hardness of the pipe.

In the preferred embodiment of the present invention, the body comprises a first cup, a second cup, and a guide rod(s)connected to the first cup at one end and to the second cup at another end. The probe is connected to the guide rod(s). The probe comprises a housing which is received by the guide rod(s) and extends transverse to the longitudinal axis of the guide rod(s), and a probe member mounted within the housing and extending transversely to the guide rod(s). An actuation means is connected to the housing for selectively urging the probe member outwardly of the housing so as to contact the pipe. Specifically, the actuation means includes a solenoid connected to the probe member for causing the probe member to move outwardly of the housing in response to a signal from a remote location. The actuation means also includes a return spring connected to the probe member so as to return the probe member to a home position when the solenoid is deactivated. In the preferred form of the present invention, the retention device includes a brake shoe which is affixed to the probe member. The brake shoe is engagable with an inner wall of the pipe so as to resist longitudinal movement of the probe member along the pipe. The retention device further includes a stop member affixed along a length of the guide rod(s). A spring extends between the stop member and the housing. The spring serves to urge the housing to a home position following the contacting of the probe with the inner surface of the pipe. The housing is slidable along the guide rod(s) between the home position and the stop member during the contacting of the probe with the inner surface of the pipe.

In an alternative form of the present invention, the probe includes a wheel which is rotatably mounted to the body. The wheel has a rim with a surface suitable for contacting the inner surface of the pipe. A probe holder is slidably mounted within the wheel. The probe holder serves to move radially outwardly and inwardly along a slot in the wheel relative to a rotation of the wheel. A probe member is mounted in the probe holder. The retention device is an arm which is slidably and pivotally connected to the body. The arm is pivotally connected at another end to the probe holder. The body has a slide bearing slidably receiving the arm such that the arm is slidable within the slide bearing when the probe contacts the inner surface of the pipe. The wheel has an axis of rotation transverse to the longitudinal axis of the body. The wheel has a hub portion and a rim portion. The rim portion has an elastomeric outer surface. The probe holder is connected to the hub portion and is offset from the axis of rotation of the wheel. A ball-and-socket joint may be used to connect the probe holder to the hub portion.

The present invention is furthermore a method of testing the hardness of the pipe which comprises the steps of: (1) forming a body having a size suitable for fitting within the pipe; (2) moving the body longitudinally through the pipe; (3) extending a hardness probe outwardly of the body so as to contact a point on an inner surface of the pipe for a desired period of time while the body moves longitudinally through the pipe; and (4) producing a signal relative to a hardness of the pipe at that point. The body moves continuously longitudinally through the pipe while the hardness probe contacts the point on the inner surface.

BRIEF DESCRIPTION OF THE DRAWINGS

FIG. is a cross-sectional side view showing the pig of the present invention as installed within a pipeline with the hardness probe shown in its retracted position.

DETAILED DESCRIPTION OF THE PRESENT INVENTION

Figure 1:
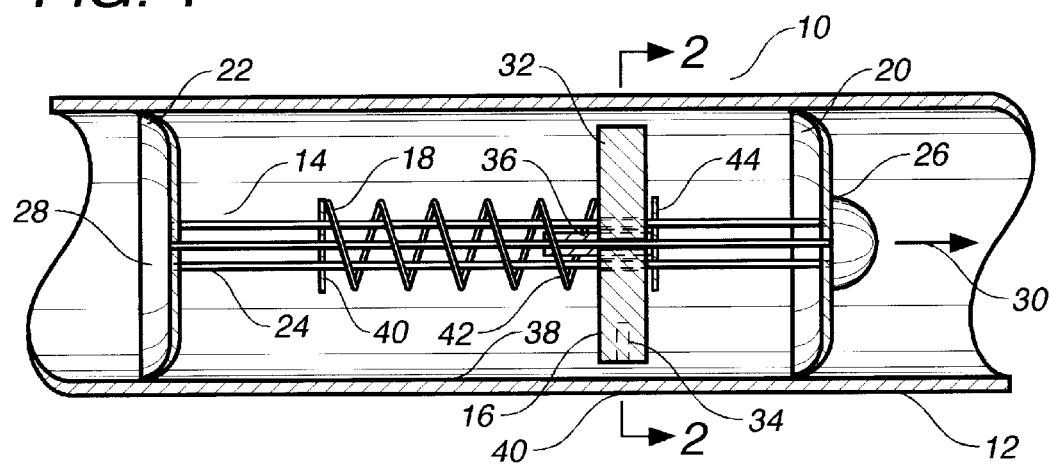

Referring to FIG. 1, there is shown at 10 the apparatus of the present invention for the testing of the hardness of a pipe 12. As shown in FIG. 1, the apparatus 10 includes a body 14 having a longitudinal axis, a probe 16 and a retaining mechanism 18. The body 14 is formed by a first cup 20, a second cup 22 and at least one guide rod 24 extending between the first cup 20 and the second cup 22. Specifically, the guide rod 24 is connected to the first cup 20 at an end 26 and is connected to the second cup 22 at another end 28. Each of the cups 20 and 22 has an outer diameter which is suitable for fitting within the inner diameter of pipe 12. The guide rod 24 or the probe mechanism 16 can be used to store the electronics, power supply and processor for the purpose of receiving information from the probe member 29 within the probe mechanism 16.

In normal use, the body 14 is installed in the pipeline 12 and moved continuously through the annulus of the pipeline 12 when a pressure of liquid or gas is pumped behind the second cup 22. This propels the body 14 forwardly continuously through the pipeline 12 in the direction of arrow 30. As will be described hereinafter, the guide rod 24 is actually three guide rods that are positioned centrally of the body 14 and offset from each other by 120 degrees. The guide rod 24 extends longitudinally in the pipe 12 and is generally in parallel axial alignment with the pipe 12.

Figure 2:
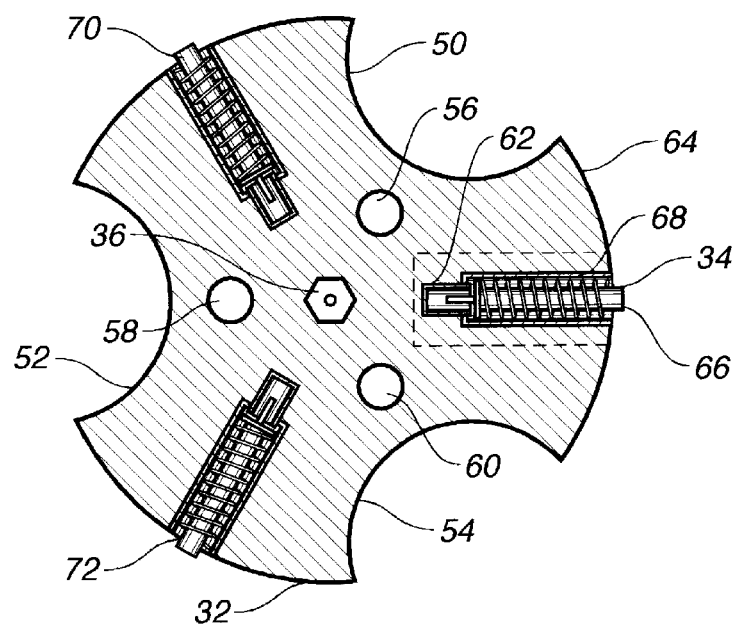
FIG. 2 is a cross-sectional view of the present invention as taken across lines 2—2 of FIG. 1.

In FIG. 1, it can be seen that the probe mechanism 16 includes a probe member 29 which extends transversely to the guide rod 24. Specifically, the housing 32 of the probe member 29 is slidably received by the guide rod 24 and extends transversely to the guide rod 24. Probe member 29 is mounted within the housing and extends transversely to the longitudinal axis of the guide rod 24. A more detailed illustration of the probe member 29 is shown in FIG. 2.

The housing 32 can suitably contain the electronics and power supply for the probe member 29. As was recited herein previously, the probe member 29, and the associated electronics, can be a MIC 10 probe. A processor can be connected to such a probe so as to convert the signals as transmitted by the probe member 29 relative to the hardness of the pipe 12 and so as to produce a humanly perceivable indication of pipe hardness. The signals can be retained in the memory within the body 14 of the apparatus 10 or the signals can be transmitted outwardly of the pipeline 12 for receipt in a remote location.

It can be seen in FIG. 1 that a stop member 40 is fixed at a desired position adjacent to the cup member 20 on the guide rod 24. The stop member 40 will serve to limit the travel of the housing 32 and the probe member 29 relative to the guide rod 24. An engaged position switch 41 is affixed on the guide rod 24 adjacent to the stop member 40.

In FIG. 1, the retention mechanism 18 includes a spring 42 that extends around the guide rod 24 and has an end contacting the surface of housing 32. The opposite end 43 of the spring 42 is engaged with or abuts a surface of the second cup member 22. Another stop member 45 is positioned between the housing 32 and the second cup member 22 and extends outwardly radially from the guide rod 24. A disconnect switch 47 is positioned adjacent to the stop member 45.

As illustrated in FIG. 1, the housing 32, with its associated probe member 29, is in a retracted position. In this position, the housing 32 and the probe member 29 will travel freely within the pipe 12. In this position, the spring 42 will urge the housing 32 in a direction toward the stop member 40 along the guide rod 24 as the device moves in the direction of arrow 30 within the pipe 12.

FIG. 2 illustrates this configuration of the housing 32. As can be seen, there are three probe members 29, 51 and 53 which are positioned so as to extend radially outwardly toward the inner surface of pipe 12. Each of these probe members 29, 51 and 53 are mounted within the housing 32. In particular, a brake shoe 55 is positioned on the side of the probe member 29. Brake shoe 55 is a resilient member which serves to establish a fixing contact with the inner wall of the pipe 12. The probe member 29 is received within a channel 57 formed in the housing 32. In particular, solenoid windings 59 are also located in the channel 57 so as to receive the end 61 of the probe member 29. An instrument return spring 63 extends around the probe member 29 so as to urge the probe member 29 to the retracted position as shown in FIG. 2. When the solenoid windings 59 are activated, as will be described hereinafter, the force of activation will overcome the resistance of the spring 63 so as to urge the probe member 29 and the associated brake shoe 55 outwardly so as to engage the inner wall of pipe 12. A suitable power supply can be configured so as to be mounted within the housing 52.

In FIG. 2, it can be seen that the housing 32 is a generally circular form of a smaller diameter than the interior of pipe 12. The housing 32 has semicircular indentations 50, 52 and 54 spaced evenly therearound. Holes 56, 58 and 60 serve to receive the guide rods 24. The holes 56, 58 and 60 should have a suitable diameter so as to allow the housing 32 to slide easily along the guide rods 24. The holes 56, 58 and 60 are offset from each other by approximately 120 degrees.

The solenoids, associated with each of the probe members 29, 51 and 53, can be powered by a conventional power pack associated with the pig onto which the body 14 is connected. A suitable power switch, such as switch 36, can be used so as to activate the solenoid windings 59 associated with probe member 29 or the solenoid windings associated with probe members 51 and 53 but pass the energy from the power pack to each of the solenoid windings when the pig apparatus has traveled a desired distance within pipe 12, as will be described hereinafter. It should be noted that the present invention can include a single probe member 29 or a plurality of probe members. The arrangement of three probe members is the preferred configuration of this form of the present invention. In other forms of the present invention, a single probe can be used with appropriate brake shoes located in the other channels within the housing 32.

Figure 3:
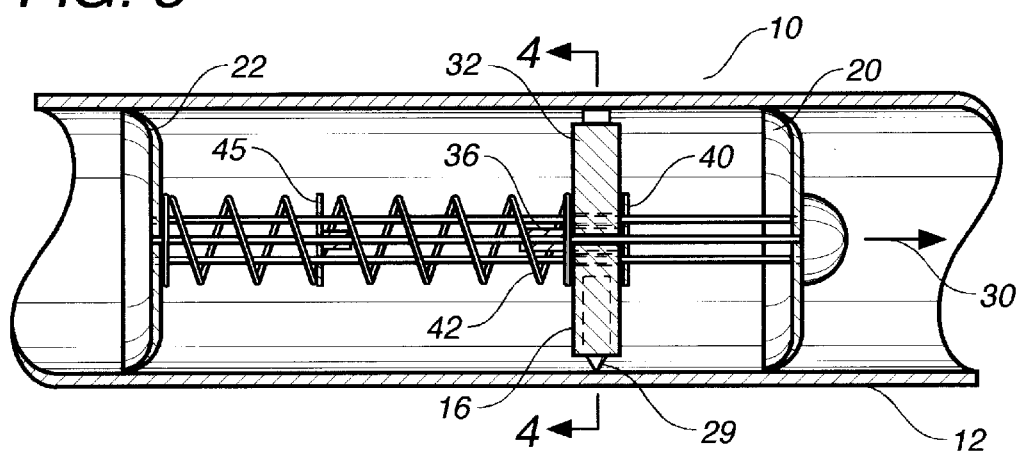
FIG. 3 is a cross-sectional side view showing the pig of the present invention as installed within a pipeline and showing the hardness probe in its testing position.
Figure 4:
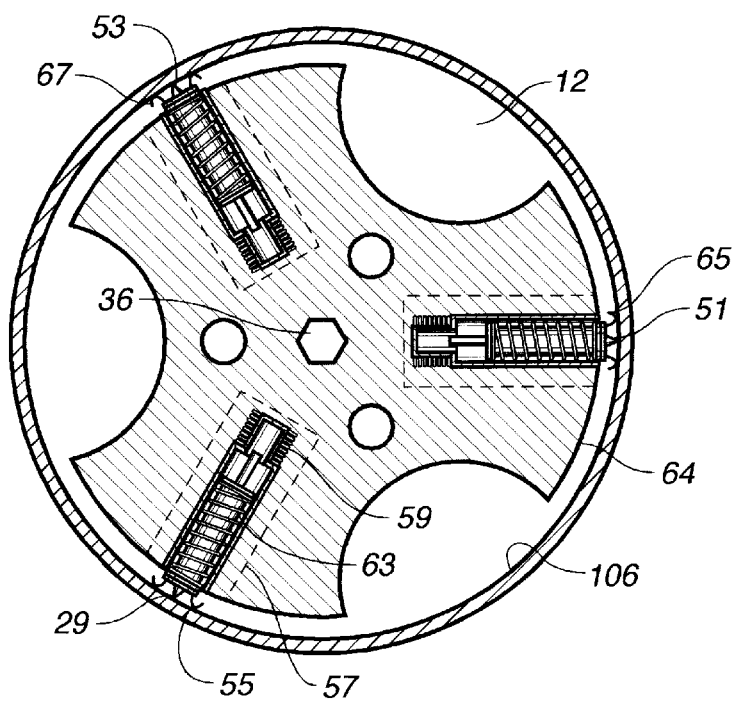
FIG. 4 is a cross-sectional view of the present invention as taken across lines 4—4 of FIG. 3.

FIGS. 3 and 4 show the operation of the present invention. In FIG. 3, it can be seen that the spring 42 has urged the housing 32 of probe member 29 in a forward direction along the guide rods 24. This forward movement occurs during the traversing of the pig apparatus 10 within the pipe 12. As such, the pig apparatus continues to move in its desired direction within the pipe 12 with no resistance by the probe mechanism 16.

Once the probe mechanism 16 and its associated housing 32 contact the stop member 40, the engaged position switch 36 is activated so as to energize the solenoids associated with probe members 29, 51 and 53. This will simultaneously activate the brake shoe 55 associated with probe member 29, the brake shoe 65 associated with probe member 51 and the brake shoe 67 associated with probe member 53. The probe member and the brake shoe will extend outwardly so as to contact the inner wall of the pipe 12. As such, a measurement of the hardness of the pipe 12 can be carried out during the forward movement of the pig apparatus 10. The engagement between the brake shoes 55, 65 and 67 and the wall of pipe 12 will assure that a suitable hardness test can be carried out by the associated probe members while the probe mechanism 16 assumes a fixed position against the inner wall of pipe 12. As such, there will be relative movement between the probe mechanism 16 and the guide rods 24 of the pig apparatus 12.

Eventually, the housing 32 will move along the guide rods 24 while the pig apparatus 10 is moving in the direction 30 within the pipe 12. As such, the probe mechanism 16, and its associated housing 32, will contact the stop member 45. This will cause an activation of the switch 36 so as to cause the spring 63 to retract the probe member 29 (along with the other probe members associated with other springs) and the brake shoe 55. As such, the probe mechanism 16 is released from the inner wall of the pipe 12 (in the manner illustrated in FIG. 1). The spring 42 will then urge the housing 32 forward along the guide rods 24 in the direction toward the first cup member 20. The present invention has an "inchworm" effect. The distance between the stop members 40 and 45 can be set relative to a desired period of hardness testing relative to the speed of the pig apparatus 10. It should be noted that the probe member 29 will be fixed against the inner wall of pipe 12 during the traversal between the stop member 40 and the stop member 45. This is carried out without any interference or reduction in speed of the pig apparatus 10 within the pipe 12.

In the operation of the present invention, when electricity is applied to the power switch 36, the solenoid is actuated so as to overcome the resistance of spring 42 and establish a measuring contact with the inner wall 106 of the pipe 12. When the power switch 36 causes the power windings 59 associated with each of the probe members to be de-energized, the spring 63 will cause the probe member 29 to retract within the channel 57. As such, the solenoid switch 36 will operate in the manner of a conventional power apparatus. Various devices can be used so as to remotely activate the power switch, such as movement sensors, timers and various related devices. The solenoid switch 36 can be powered in a known manner by a conventional battery pack located in the pig apparatus. The switch will cause to serve power to be passed from the battery pack so as to energize the solenoid or to cause the solenoid to be de-energized by removing from the solenoid in the manner of conventional solenoids.

It is important to note that the housing 32 contains hardness probes 29, 51 and 53 located at 120 degrees to each other. Each of these probes 29, 51 and 53 are simultaneously actuated by three separate solenoids 59 associated with each of the probes. The switch 36 will serve to actuate each of the solenoids so that each of the probes 29, 51 and 53, along with their associated and respective brake shoes 55, 65 and 67, outwardly of the outer surface 64 of the housing 32. Each of the probes 51 and 53 will have an identical configuration to that of probe member 29. The static time required to obtain the test is the time that the pig apparatus 10 takes to travel between the stops 40 and 45. This distance can be adjusted to obtain the optimum static time of the probe mechanism relative to the pipe 12 in order for the hardness testing device to make a valid measurement. The measurement is digitally recorded on the on-board memory after each cycle of the apparatus 10. It is important to note that the body 14 and/or the housing 32 can incorporate various other sensors, such as eddy current, magnetism and sound velocity sensors.

Figure 5:
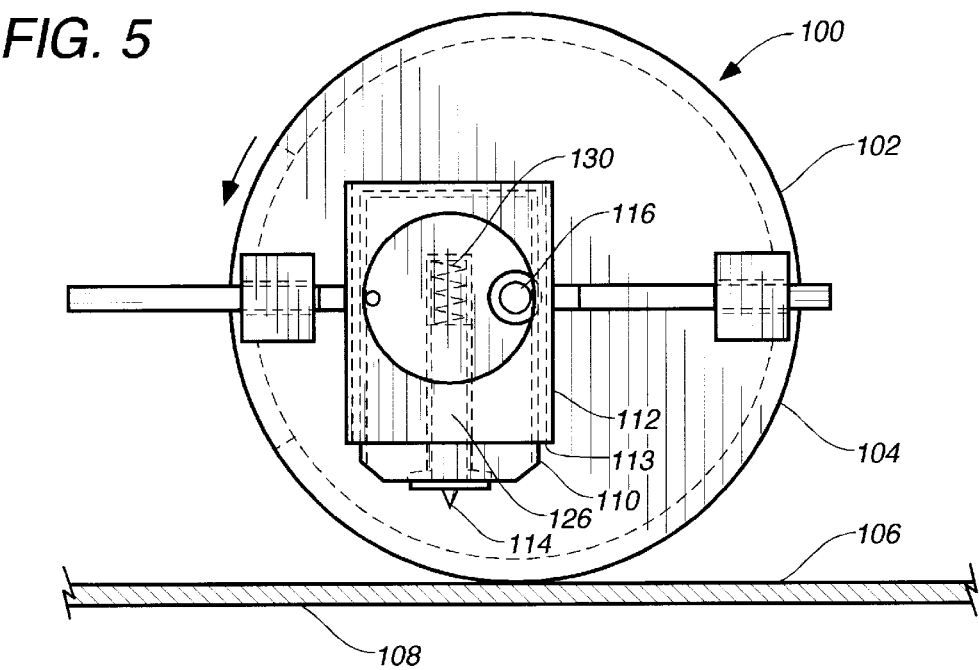
FIG. 5 is a cross-sectional side view showing an alternative form of the present invention and as showing the hardness probe in a retracted position.

FIGS. 5–10 show an alternative embodiment of the hardness testing apparatus 100 of the present invention. As can be seen in FIG. 5, the hardness testing apparatus 10 includes a wheel 102 having an elastomeric outer surface 104 that rides against the inside wall 106 of a pipe line 108. A probe holder 110 is mounted within a housing 112 having a receiving slot 113 therein. The housing 112 is mounted in the wheel 102 such that the probe tip 114 will contact the surface 106 during a rotation of the wheel 102.

Figure 6:
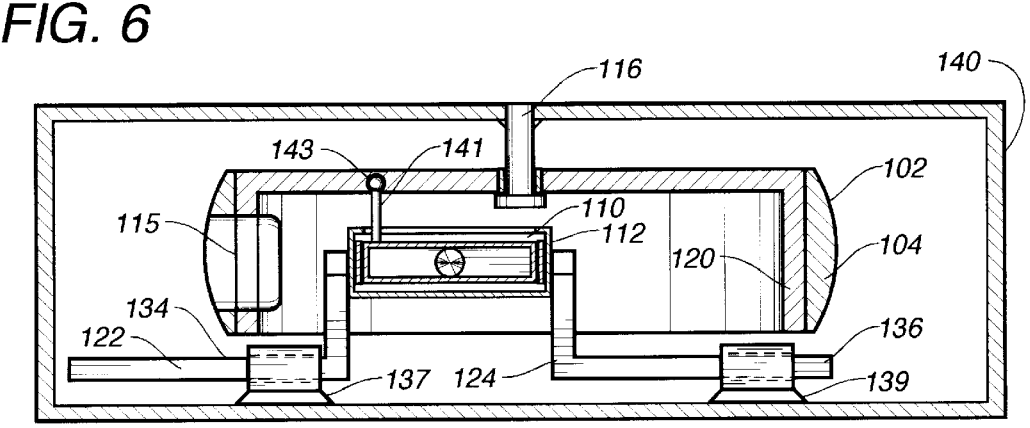
FIG. 6 is a cross-sectional plan view of the apparatus as shown in FIG. 5.

Referring to FIG. 6, it can be seen that the wheel 102 has an elastomeric outer surface 104 suitable for riding along the inner wall of the pipeline 108. An outer enclosure 140 extends around the wheel 102. It can be seen that the wheel 102 has a diameter which is less than the length of the interior of the enclosure 140. The wheel 102 has a generally C-configuration with a window 115 formed along the outer diameter of the wheel 102. The wheel 102 has an outer diameter 104 which is set such that it is in contact with a surface of the inside wall 106 of pipeline 108. The wheel 102 is mounted to an axle 116 which is supported, at one end, on the enclosure 140 and extends such that the wheel rotates therearound. The axis of the wheel is set to follow the axis of the pipeline 108. The window 115 is cut into the rim 120 of the wheel 102 so as to allow the probe tip 114 to gain access to the pipe wall 106. The rim 120 of the wheel 102 is wide enough to permit the contoured hard rubber tire surface 104 to maintain smooth contact with the pipe wall 106 as the window section 115 rotates along the wall 106 of pipeline 108. Guide mount rods 122 and 124 are connected to the slotted housing 112. Each of the guide mount rods 122 and 124 have linear sections 134 and 136 which are slidably received within slide receptacles 137 and 139. Slide receptacles 137 and 139 are fixedly mounted to an inner wall of the enclosure 140. The guide mount rods 122 and 124 preferably have a square cross section. Similarly, the slotted interior area of the receptacles 137 and 139 should be slightly larger than the cross-sectional area of the linear portions 134 and 136 so as to allow the guide mount rods 122 and 124 to slide back and forth therethrough as the housing 112 moves back and forth within the interior of the wheel 102 during the movement of the enclosure 140 within the pipeline 108.

In FIG. 6, it can be seen that the probe holder 110 is pivotally connected by an arm 141 to a ball-and-socket joint 143. The ball-and-socket joint 143 is cantably received within the wall 145 of the wheel 142. The opposite end of the arm 141 is rotatably connected to the probe holder 110 so as to allow the probe holder 110 to move upwardly and downwardly within the housing 102 during the rotation of the wheel 102. The sequence of timing between the respective components of the wheel 102 is such that, during a rotation of the wheel 102, the probe holder 110, as sequenced with the housing 112, will move downwardly so that the probe 114 will pass outwardly through the window 115 so as to contact the inner wall 106 of pipe 108. Probe holder 110 will move upwardly and downwardly within the slotted area 113 of housing 112 relative to the rotation of the wheel 102. The ball-and-socket joint 143, connected between the probe holder 110 and the wall 145 of the wheel 102, facilitates the upward and downward movement of the probe holder 110. The probe holder 110 and the slotted housing 112 serve to convert the rotational movement of the wheel 102 into a rectilinear movement. Spring 130 is provided on the end of the probe instrument 126 so as to urge the probe 114 outwardly.

Figure 7:
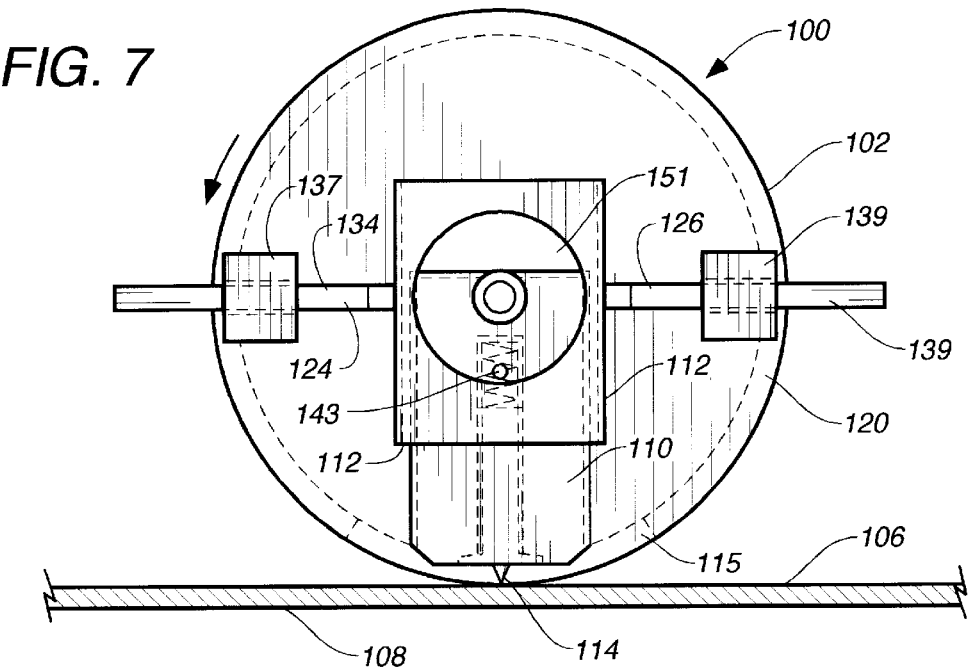
FIG. 7 is a cross-sectional side view showing the alternative form of the present invention with the hardness probe in a testing position.
Figure 8:
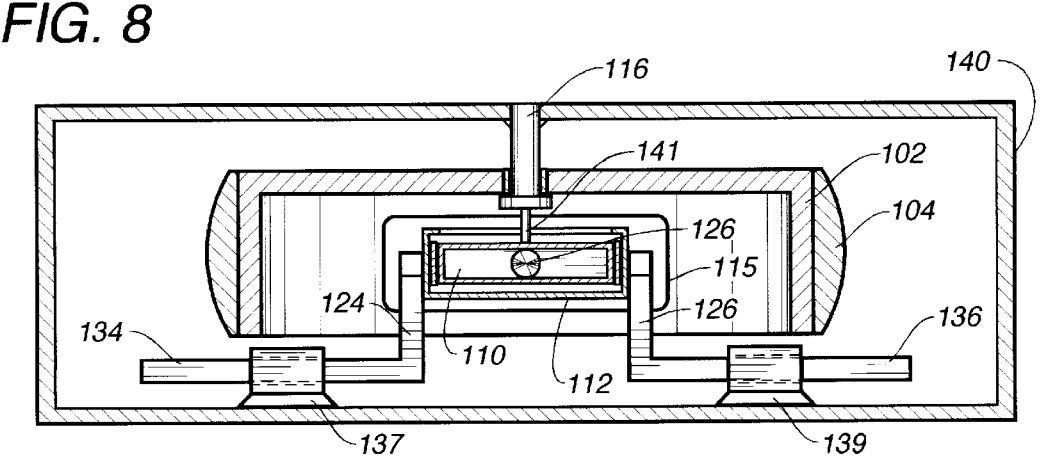
FIG. 8 is a cross-sectional plan view of the apparatus as shown in FIG. 7.

FIG. 7 shows how the probe holder 110 is moved outwardly of the housing 112 so as to allow the probe 114 to contact the inner wall 106 of the pipeline 108. FIG. 8 shows a plan view of this arrangement.

Referring to FIGS. 7 and 8, it can be seen how the linear members 134 and 136 associated with the guide mount rods 124 and 126 have moved within the receptacles 137 and 139. For the purposes of illustration, the receptacles 137 and 139 are illustrated in their desired position. To avoid confusion, the enclosure 140 is not shown in FIG. 7. The window area 115 open through the rim 120 at the area of the inner wall 106 of pipeline 108. At the same time, the ball-and-socket joint 143 associated with the arm 141 is shown as rotated to its lowermost position with respect to retainer wheel 151. This, concomitantly, causes the probe holder 110 to be moved to its lowermost position with respect to the slotted interior 113 of the housing 112. The spring 130 assures that the probe 104 will reside in contact with the inner wall 106 for a desired period of time during the rotation of the wheel 102.

In FIG. 8, it can be seen that the axle 116 remains in its fixed position with respect to the enclosure 140. The wheel 102 will rotate freely around axle 116 while the remaining linkages cause the probe holder 110 to move upwardly and downwardly with respect to the rotation of the wheel 102.

Figure 9:
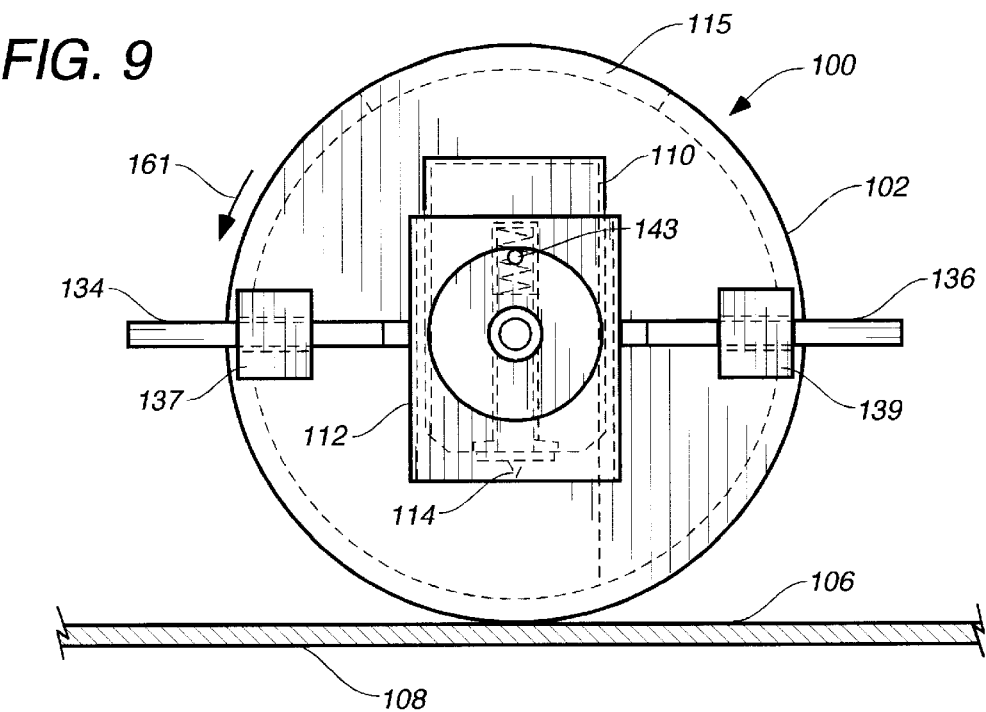
FIG. 9 is a cross-sectional side view of the alternative form of the present invention as showing the hardness probe in a retracted position.

FIG. 9 shows further how the apparatus 100 operates during the rotation of the wheel 102 with respect to the wall 106 of pipeline 108. In FIG. 9, the window 115 is moved 180 degrees away from the wall 106. In this position of rotation, the probe holder 110 will be in its uppermost position by virtue of the rotation of the ball-and-socket joint 143 and its associated arm 141. As such, the probe 114 will be fully retracted within the housing 112. As the wheel 102 rotates in the direction of arrow 161, the linear members 134 and 136 will move to the left through the receptacles 137 and 139. This will cause the housing 112 to concomitantly move toward the left. The rotation of the wheel will slowly cause the probe holder 110 to move downwardly within the housing 112 until such time as the window 115 will reside against the inner wall 106 of pipeline 108. As such, a proper measurement can be taken in this position.

Figure 10:
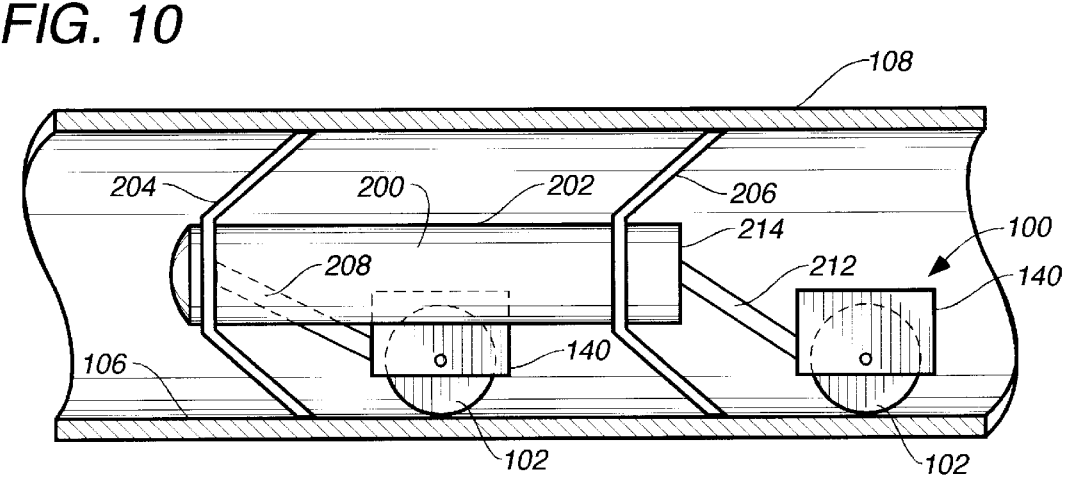
FIG. 10 is a diagrammatic illustration of the alternative form of the apparatus of the present invention as attached to a pig.

FIG. 10 illustrates the use of this alternative embodiment 100 of the present invention inn the pipeline 108 as associated with a pig 200. As can be seen, the pig 200 has a body 202 which is positioned within the interior of the pipeline 108. Cup members 204 and 206 serve to retain the pig body 202 in its desired position within the pipeline 108. In one form of the present invention, the enclosure 140 associated with wheel 102 can be positioned within the pig body 202 between the cup members 204 and 206. A torsion bar or leaf spring 208 can extend from the pig body 202 to the housing 140. The torsion bar 208 is necessary so that the wheel 102 will contact the inner wall 106 of pipeline 108 with a desired force. In other words, the torsion bar 208 will urge the wheel 102 radially outwardly from the pig body 202.

FIG. 10 also shows an alternative form of the present invention in which the housing 140 and the associated wheel 102 of this alternative embodiment 100 of the present invention trails behind the pig body 202 and behind the second cup 206. A torsion bar 212 extends from the rear 214 of pig body 202 and is connected to the enclosure 140. Torsion bar 212 operates similarly so as to urge the wheel 102 against the wall 106 of pipeline 108.

In this alternative embodiment of the present invention, as the ball-and-socket joint 143 drives the probe holder 110 past the horizontal, the probe 114 is forced to move downwardly. The probe 114 is constrained from rotating so as to push the probe 114 against the wall 106 of the pipeline 108. The spring 130 located at the top of the probe 114 allows the probe 114 to push against the wall 106. The combination of the horizontal sliding and vertical sliding within the mechanism of apparatus 100 converts the rotation of wheel 102 into rectilinear motion. The spring 130 keeps the probe 114 in contact with the wall 106. The result of the above is to place the probe in static contact with the wall of the pipeline and to hold it there for approximately one inch of travel of the pig 200. As such, the present invention has a "timing" effect which occurs during the rotation of the wheel 102.

Within the concept of the present invention, the pig apparatus, in either of the embodiments, can incorporate electrical conductivity and velocity of sound as further measurements of the respective pipelines. As such, it is possible to further compare unknown joints of pipe to known joints of pipe in a pipeline. The present invention is intended as an improvement to or an addition to an existing pig apparatus. The improvement of the present invention is the incorporation of the hardness test in a manner which can easily and simply obtain hardness information as to the nature and quality of the pipeline.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

We claim:

1. An apparatus for testing hardness of a pipe comprising:

a body having a longitudinal axis;

a probe connected to said body and extending transverse to said longitudinal axis, said probe adapted to contact an inner surface of the pipe so as to produce a signal relative to a hardness of the pipe;

a retainer means connected to said probe and positioned within said body, said retainer adapted to maintain said probe in a fixed position relative to the pipe while said body is moving in the pipe; and processor connected to said probe and adapted to convert said signal to a humanly perceivable indication of pipe hardness.

2. The apparatus of claim 1, said body comprising:

a first cup;

a second cup; and a guide rod connected to said first cup at one end and to said second cup at another end, said probe being connected to said guide rod.

3. The apparatus of claim 2, further comprising:

an actuator connected to said body, said actuator adapted to selectively moving said probe outwardly of said body so as to contact the pipe.

4. The apparatus of claim 3, said actuator comprising:

a solenoid connected to said probe and adapted to cause said probe to move outwardly of said body in response to a signal from a remote location; and a return spring connected to said probe so as to return said probe to a home position when said solenoid is deactivated.

5. The apparatus of claim 2, said retainer means comprising:

a brake shoe affixed to said probe, said brake shoe engagable with an inner wall of the pipe so as to resist longitudinal movement of said probe along the pipe.

6. The apparatus of claim 2, said retainer comprising:

a stop member affixed along a length of said guide rod; and a spring extending between said stop member and said body, said spring urging said body to a home position following the contacting of said probe with the inner surface of the pipe.

7. The apparatus of claim 6, said body slidably along said guide rod between said home position and said stop member during the contacting of said probe with the inner surface of the pipe.

8. The apparatus of claim 2, said guide rod comprising:

a first guide rod slidably connected to said body;

a second guide rod slidably connected to said body; and a third guide rod slidably connected to said body, said first; second and third guide rods having longitudinal axes in parallel relation to each other, said first, second and third guide rods being offset from each other by 120°.

9. The apparatus of claim 8, said probe comprising:

a first probe member mounted within said body and extending transverse to said longitudinal axes of the guide rod;

a second probe member mounted within said body and offset by approximately 120° from said first probe member, said second probe member extending transverse to said longitudinal axes of the guide rod; and a third probe member mounted within said body and offset by approximately 120° from said first and second probe members, said third probe member extending transverse to said longitudinal axes of the guide rod, each of said first, second and third probe members being simultaneously actuable so as to contact the inner surface of the pipe.

10. The apparatus of claim 1, further comprising:

a wheel rotatably mounted to said body, said wheel having a rim with a surface suitable for contacting the inner surface of the pipe;

a housing having a slotted interior; and a probe holder slidably received within said wheel, said probe holder movable radially outwardly of said slotted interior of said housing relative to a rotation of said wheel said probe mounted in said probe holder.

11. The apparatus of claim 10, said retainer comprising:

an arm slidably and pivotally connected to said body, said arm pivotally connected at another end to said probe holder.

12. The apparatus of claim 10, said wheel having an axis of rotation transverse to said longitudinal axis of said body.

13. The apparatus of claim 10, said wheel having a wall and a rim portion, said rim portion having an elastomeric outer surface, said probe holder being connected to said wall in a position offset from an axis of rotation of said wheel.

14. The apparatus of claim 13, said probe holder comprising:

a ball-and-socket means having one end cantably connected to said wall, said ball-and-socket having an arm extending therefrom, said ball-and-socket adapted to move said probe holder rectilinearly within said housing relative to a rotation of said wheel.

15. A method of testing the hardness of a pipe comprising the steps of:

forming a body having a size suitable for fitting within the pipe;

moving the body longitudinally through the pipe;

extending a hardness probe outwardly of said body so as to contact a point on an inner surface of the pipe for a desired period of time while said body moves longitudinally through the pipe; and producing a signal relative to a hardness of the pipe at said point.

16. The method of claim 15, said body moving continuously longitudinally through said pipe while said hardness probe contacts said point on said inner surface.

17. The method of claim 16, further comprising the steps of:

sliding said hardness probe within said body while said body moves continuously through the pipe.

18. The method of claim 15, further comprising the step of:

processing the signal so as to convert said signal into a humanly perceivable indication of hardness.

* * * * *